United States Patent [19]

Onodera et al.

[11] Patent Number: 4,966,896
[45] Date of Patent: Oct. 30, 1990

[54] DERIVATIVE OF N-METHYLCARBAMATE AND INSECTICIDE CONTAINING THE SAME

[75] Inventors: Nobuo Onodera; Katsumi Nanjo; Akinori Kariya; Kiyoshi Kanase, all of Tokorozawa, Japan

[73] Assignee: Agro-Kanesho Company, Ltd., Tokyo, Japan

[21] Appl. No.: 369,527

[22] Filed: Jun. 21, 1989

[30] Foreign Application Priority Data

Aug. 18, 1988 [JP] Japan .................... 63-205607

[51] Int. Cl.$^5$ .................... A01N 43/12; C07D 307/86
[52] U.S. Cl. .................... 514/469; 514/337; 514/370; 546/269; 548/194; 549/470
[58] Field of Search .................... 549/470; 548/194; 546/269; 514/337, 370, 469

[56] References Cited

U.S. PATENT DOCUMENTS

| | | | |
|---|---|---|---|
| 4,006,231 | 2/1977 | Black et al. | 424/248.5 |
| 4,302,466 | 11/1981 | Heywang et al. | 544/58.4 X |
| 4,344,883 | 8/1982 | Fahmy et al. | 549/467 |
| 4,532,256 | 7/1985 | Drabek et al. | 514/469 |

Primary Examiner—Richard L. Raymond
Attorney, Agent, or Firm—Oblon, Spivak, McClelland, Maier & Neustadt

[57] ABSTRACT

An insecticide having high insecticidal activities against various harmful insects, which is low in toxicity to warm-blooded animals and fishes to be used safely. The insecticide comprises a derivative of 2,3-dihydro-2,2-dimethylbenzofuran-7-yl N-(substituted sulfonylcarbamoyl)-N-methylcarbamate represented by the general formula:

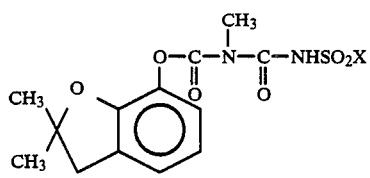

wherein X stands for a halogen atom; —NHR where R is an alkyl group, cycloalkyl group, lower alkenyl group, lower alkynyl group or

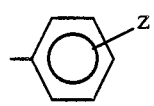

(where Z is a hydrogen atom, halogen atom, alkyl group, alkoxy group or alkoxycarbonyl group), aralkyl group, a 5-member or 6-member heterocyclic group, or an alkoxy group.

12 Claims, No Drawings

DERIVATIVE OF N-METHYLCARBAMATE AND INSECTICIDE CONTAINING THE SAME

BACKGROUND OF THE INVENTION

1. Field of the Invention

The present invention relates to a derivative of 2,3-dihydro-2,2-dimethylbenzofuran-7-yl N-(substituted sulfonylcarbamoyl) N-methylcarbamate represented by the general formula:

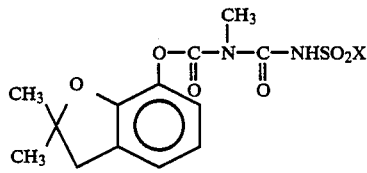

wherein X stands for a halogen atom; —NHR where R is an alkyl group, cycloalkyl group, lower alkenyl group, lower alkynyl group or

(where Z is a hydrogen atom, halogen atom, alkyl group, alkoxy group or alkoxycarbonyl group), aralkyl group, a 5-member or 6-member heterocyclic group, or an alkoxy group.

It further relates to a process for preparing the derivative of N-methylcarbamate described above, and an insecticide containing the same as an effective component.

2. Prior Art Statement 2,3-dihydro-2,2-dimethylbenzofuran-7-yl N-methylcarbamate (generally referred to hereinafter as carbofuran) is a useful compound as an insecticide since it has high insecticidal effect against a broad range of insects and long lasting effect. However, it is extremely toxic to warm-blooded animals and fishes, and thus it entails problems in use which decrease its practical utility. Research toward reducing the toxicity of carbofuran has led to many patent applications relating to the compounds of this group, including the following:

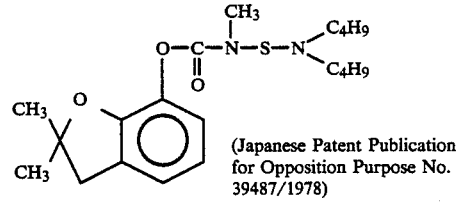

(Japanese Patent Publication for Opposition Purpose No. 39487/1978)

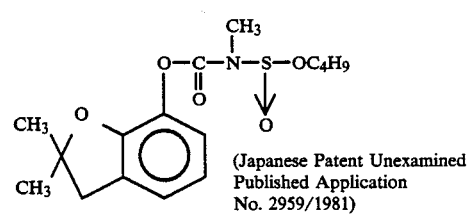

(Japanese Patent Unexamined Published Application No. 2959/1981)

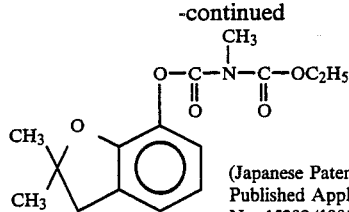

(Japanese Patent Unexamined Published Application No. 15280/1981)

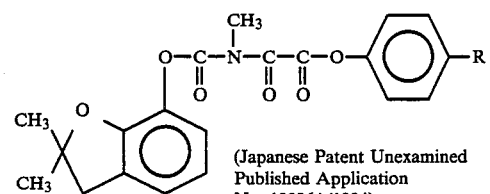

(Japanese Patent Unexamined Published Application No. 130264/1984)

However, only two of the published compounds have been practically used as insecticides, and even these practically used compounds are not satisfactory.

OBJECT AND SUMMARY OF THE INVENTION

An object of this invention is to provide a novel compound which has high insecticidal activity to control various harmful insects and is low in toxicity to warm-blooded animals and fishes and is stable when used as an effective component in a novel insecticide.

Another object of this invention is to provide a process for preparing the novel compound described above.

A further object of this invention is to provide a novel insecticide which has high insecticidal activity to control various harmful insects and is low in toxicity to warm-blooded animals and fishes and is stable over long periods.

Through research toward the development of useful insecticides by the use of derivatives of carbofuran, we have found that the compounds of this invention have high insecticidal activities and useful properties when used as insecticides.

According to a first aspect of this invention, there is provided a derivative of 2,3-dihydro-2,2-dimethylbenzofuran-7-yl N-(substituted sulfonylcarbamoyl) N-methylcarbamate represented by the general formula:

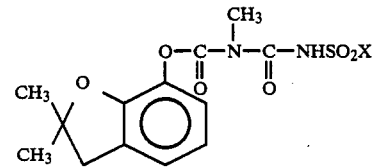

wherein X stands for a halogen atom; —NHR where R is an alkyl group, cycloalkyl group, lower alkenyl group, lower alkynyl group or

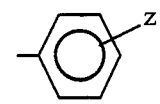

(where Z is hydrogen atom, halogen atom, alkyl group, alkoxy group or alkoxycarbonyl group), aralkyl group, a 5-member or 6-member heterocyclic group, or an alkoxy group.

Also provided by this invention is a process for preparing a derivative of 2,3-dihydro-2,2-dimethylbenzofuran-7-yl N-(halogeno-sulfonylcarbamoyl)-N-methylcarbamate represented by the general formula:

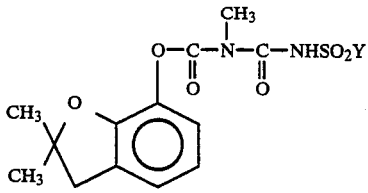

wherein Y stands for a halogen atom; comprising the step of reacting 2,3-dihydro-2,2-dimethylbenzofuran-7-yl N-methylcarbamate represented by the formula:

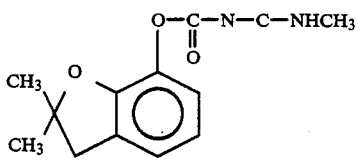

with a halogenosulfonylisocyanate represented by the general formula:

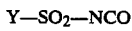

Y—SO₂—NCO wherein Y stands for a halogen atom.

Further provided by this invention is a process for preparing a derivative of 2,3-dihydro-2,2-dimethylbenzofuran-7-yl N-(substituted sulfamoylcarbamoyl)-N-methylcarbamate represented by the general formula:

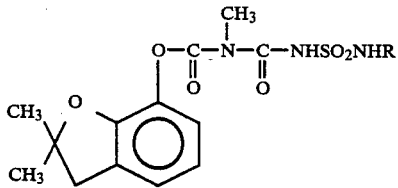

wherein R stands for an alkyl group, cycloalkyl group, lower alkenyl group, lower alkynyl group or

(where Z is a hydrogen atom, halogen atom, alkyl group, alkoxy group or alkoxycarbonyl group), aralkyl group, a 5-member of 6-member heterocyclic group, or an alkoxy group, comprising the step of reacting a derivative of 2,3-dihydro-2,2-dimethylbenzofuran-7-yl N-(halogenosulfonylcarbamoyl)-N-methylcarbamate represented by the general formula:

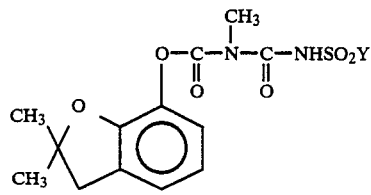

wherein Y stands for a halogen atom with an amine represented by the general formula:

R—NH₂ wherein R is the same as defined above.

According to a further aspect of this invention, there is provided an insecticide containing as an effective component a derivative of 2,3-dihydro-2,2-dimethyl-benzofuran-7-yl N-(substituted sulfonylcarbamoyl)-N-methylcarbamate represented by the general formula:

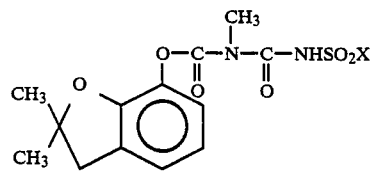

wherein X stands for a halogen atom: —NHR where R is an alkyl group, cycloalkyl group, lower alkenyl group, lower alkynyl group or

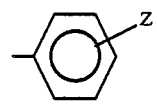

(where Z is a hydrogen atom, halogen atom, alkyl group, alkoxy group or alkoxycarbonyl group), aralkyl group, a 5-member or 6-member heterocyclic group, or an alkoxy group.

DESCRIPTION OF THE INVENTION

The compound of this invention is a novel compound which has not been described in any prior publication and was synthesized by us for the first time.

The compound of this invention has a high insecticidal activity and long lasting effect against harmful insects including Coleoptera such as Beetles, Rice water weevil (*Lissophoptrus oryzophilus*) and Twenty-eight-spotted ladybird (*Epilachna vigintioctopunctata*), Lapidoptera such as Armyworms, Common white (*Pieris rapae*), Diamondback moth (*Plutella xylostella*) and Semi-loopers, Hemiptera such as Planthoppers, Leafhoppers, White flies and Aphids, Thysanoptera such as Thrips palmi and Onion thrips (*Thrips tabaci*) and Plant parasitic nematodes such as Root-knot nematodes and Root-lesion nematodes. The acute toxicities of the compounds of this invention to warm-blooded animals are extremely low, several tens of times lower than that of carbofuran so that they are very useful as insecticides. The compounds of this invention can be easily and economically prepared and are thus preferable from an industrial point of view.

Typical examples of the compounds of this invention are set out forth below.

2,3-dihydro-2,2-dimethylbenzofuran-7-yl N-(methylsulfamoylcarbamoyl) N-methylcarbamate;
2,3-dihydro-2,2-dimethylbenzofuran-7-yl N-(ethylsulfamoylcarbamoyl) N-methylcarbamate;
2,3-dihydro-2,2-dimethylbenzofuran-7-yl N-(propylsulfamoylcarbamoyl) N-methylcarbamate;
2,3-dihydro-2,2-dimethylbenzofuran-7-yl N-(isopropylsulfamoylcarbamoyl) N-methylcarbamate;
2,3-dihydro-2,2-dimethylbenzofuran-7-yl N-(butylsulfamoylcarbamoyl) N-methylcarbamate;
2,3-dihydro-2,2-dimethylbenzofuran-7-yl N-(cyclohexylsulfamoylcarbamoyl) N-methylcarbamate;
2,3-dihydro-2,2-dimethylbenzofuran-7-yl N-(allylsulfamoylcarbamoyl) N-methylcarbamate;
2,3-dihydro-2,2-dimethylbenzofuran-7-yl N-(propargylsulfamoylcarbamoyl) N-methylcarbamate;
2,3-dihydro-2,2-dimethylbenzofuran-7-yl N-(phenylsulfamoylcarbamoyl) N-methylcarbamate;
2,3-dihydro-2,2-dimethylbenzofuran-7-yl N-(2-chlorophenylsulfamoylcarbamoyl) N-methylcarbamate;
2,3-dihydro-2,2-dimethylbenzofuran-7-yl N-(2-methylphenylsulfamoylcarbamoyl) N-methylcarbamate;
2,3-dihydro-2,2-dimethylbenzofuran-7-yl N-(2-methoxyphenylsulfamoylcarbamoyl) N-methylcarbamate;
2,3-dihydro-2,2-dimethylbenzofuran-7-yl N-(2-methoxycarbonylphenylsulfamoylcarbamoyl) N-methylcarbamate;
2,3-dihydro-2,2-dimethylbenzofuran-7-yl N-(4-ethoxycarbonylphenylsulfamoylcarbamoyl) N-methylcarbamate;
2,3-dihydro-2,2-dimethylbenzofuran-7-yl N-(benzylsulfamoylcarbamoyl) N-methylcarbamate;
2,3-dihydro-2,2-dimethylbenzofuran-7-yl N-(2-thiazolylsulfamoylcarbamoyl) N-methylcarbamate;
2,3-dihydro-2,2-dimethylbenzofuran-7-yl N-(2-pyridylsulfamoylcarbamoyl) N-methylcarbamate;
2,3-dihydro-2,2-dimethylbenzofuran-7-yl N-(methoxysulfamoylcarbamoyl) N-methylcarbamate.

The compounds of this invention may be synthesized by the reaction represented by the following reaction equation. In the following reaction equation, Y and R have the same meaning as defined earlier.

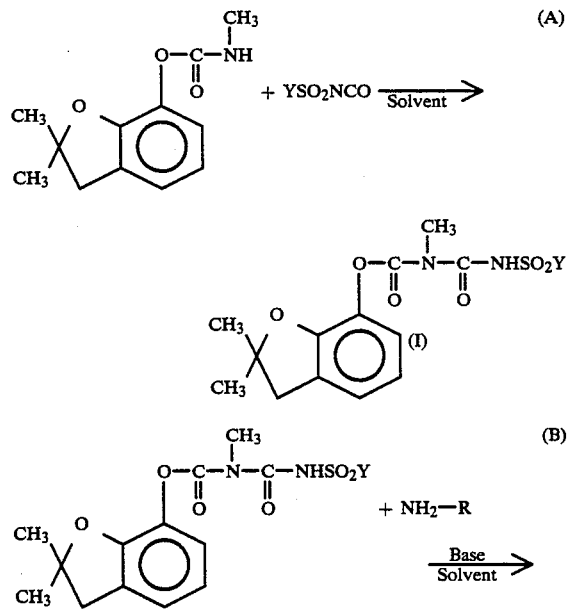

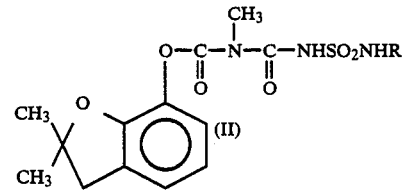

In the reaction represented by the reaction equation (A), it is preferred that Y in the compound $YSO_2NCO$ be chlorine or bromine atom, chlorine atom being particularly preferred. The amount of used $YSO_2NCO$ is preferably equal to or slightly in excess of the molecular equivalent of carbofuran, and generally ranges from 1.0 to 1.1 mols to 1 mol of carbofuran. A preferable solvent is an anhydrous inert solvent, examples being ethers such as tetrahydrofuran and dioxane, esters such as ethyl acetate, halogenated hydrocarbons such as dichloromethane and chloroform, aromatic hydrocarbons such as benzene and chlorobenzene, and polar solvents such as dimethylformamide. These solvents may be used alone or in combination. The amount of the used solvent is not particularly limited, and the volume of the used solvent ranges generally 5 to 20 times of the weight of carbofuran.

The reaction may be performed at a temperature of from −(minus) 10° C. to a temperature higher than room temperature, preferably from 0° to 40° C.

The reaction time varies on the reaction condition, and the reaction is completed generally within 1 to 10 hours.

The reaction product may be refined by using a proper solvent after removing the reaction solvent from the reaction mixture and may be used in the subsequent reaction (B), but the reaction mixture may be used directly in the subsequent reaction (B) without subjecting the same to any after-treatment.

It is preferred that an excess amount of amine represented by $R—NH_2$ be added to the sulfamoylhalogenide prepared by the reaction (A) and represented by the formula (I) to perform the reaction (B), generally 1.05 to 1.8 mols of $R—NH_2$ being added to 1 mol of the sulfamoylhalogenide. 2 mols or more of amine may be added to 1 mol of the sulfamoylhalogenide so that the excess amine acts as a deacidic agent.

Similar solvents as used in the reaction (A) may be used in the reaction (B). A solution of an amine dissolved in water or an alcohol may also be used in the reaction (B).

Examples of the base which may be used in the reaction (B) are tertiary amines such as triethylamine and pyridine, and inorganic bases such as potassium carbonate, sodium hydroxide and sodium bicarbonate. It is convenient to use the base in excess of the quantity of sulfamoylhalogenide represented by the formula (I), and it is preferred that 2.0 to 4.0 mols of base be used per 1 mol of sulfamoylhalogenide.

The reaction temperature may be set within a range of from −(minus) 10° C. to a temperature of higher than room temperature, preferably from 0° to 30° C. The reaction time varies on the reaction condition, and the reaction is completed generally within 10 hours.

Examples of usable amines represented by the general formula $R—NH_2$ include aliphatic amines such as methylamine, ethylamine, propylamine, isopropylamine, butylamine, hexylamine, cyclohexylamine, allylamine and propargylamine, aryl amines such as aniline, chloroaniline, toluidine, anisidine and aminobenzoic ester, aralkyl amines such as benzylamine, hetrocyclic amines such as 2-aminothiazole, aminopyridine, and alkoxylamines such as methoxyamine.

The reaction product (II) of the reaction (B) may be isolated from the reaction mixture by an ordinary method, and may be easily refined through recrystallization or column chromatography, as desired.

The process for the preparation of the compounds of this invention will be described hereinbelow by referring to some Examples. However, it is noted here that the invention is not limited by the following Examples. In the following Examples, the infrared absorption spectra of the resultant compounds will be shown only partially.

EXAMPLE 1

2,3-Dihydro-2,2-dimethylbenzofuran-7-yl N-(chlorosulfonylcarbamoyl) N-methylcarbamate (Compound No. 1)

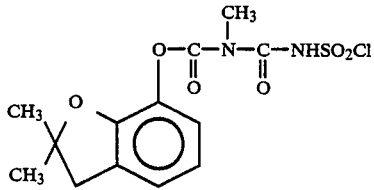

A solution of 1.45 g of chlorosulfonylisocyanate in 4 ml of dichloromethane was added slowly to a solution of 2.21 g of carbofuran in 15 ml of dichloromethane at a temperature of lower than 10° C. under stirring. After reacting for about an hour, the temperature of the reaction mixture was raised to room temperature and the reaction was continued for additional 4 hours. Then, the solvent was recovered under reduced pressure to obtain 4.20 g of a viscous product. The viscous product was refined from a solvent of ether:hexane=1:2 to obtain an objective compound having a decomposition temperature of 114° to 115.5° C. in the form of a white crystal.

Infrared Absorption Spectrum (KBr Method) 1743 cm$^{-1}$, 1335 cm$^{-1}$, 1167 cm$^{-1}$.

EXAMPLE 2

2,3-Dihydro-2,2-dimethylbenzofuran-7-yl N-(methylsulfamoylcarbamoyl) N-methylcarbamate (Compound No. 2)

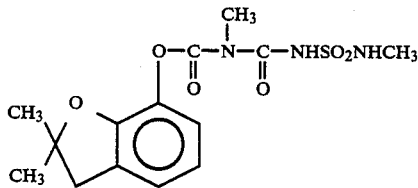

0.48 g of a 40% aqueous solution of methylamine and 1.11 g of triethylamine were added to 10 ml of dichloromethane, and a solution of 1.81 g of the compound prepared by Example 1 in 10 ml of dichloromethane was added gradually to the above amine solution at a temperature of lower than 10° C. under sufficient stirring. After the lapse of about an hour, the temperature of the reaction mixture was raised to room temperature and the reaction was continued for 3 hours. The solvent was recovered under reduced pressure and the residue was dissolved in acetone, added with 100 ml of water and then added with hydrochloric acid to adjust the pH of the reaction mixture to the weakly acidic region, whereby a crystal was separated. The crystal was filtered, washed with water and dried to obtain 1.20 g of a crude crystal. The crude crystal was refined from a solvent of ether:hexane=5:1 to obtain an objective compound having a melting point of 142° to 143° C. in the form of a white crystal.

Infrared Absorption Spectrum (KBr Method) 1737 cm$^{-1}$, 1338 cm$^{-1}$, 1167 cm$^{-1}$

EXAMPLE 3

2,3-Dihydro,2,2-dimethylbenzofurane-7-yl N-(ethylsulfamoylcarbamoyl) N-methylcarbamate (Compound No. 3)

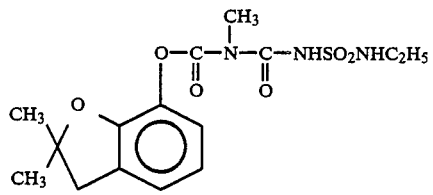

Similarly as in Example 1, a solution of Compound No. 1 in dichloromethane was prepared by using 1.11 g of carbofuran. The solution in dichloromethane was added slowly to a solution obtained by mixing 0.42 g of a 70% aqueous solution of ethylamine, 1.11 g of triethylamine and 5 ml of tetrahydrofuran at a temperature of lower than 10° C. After the lapse of about an hour, the temperature of the reaction mixture was raised to room temperature to continue the reaction for an additional 3 hours, and then dichloromethane was added to the reaction mixture, and washed initially with a dilute hydrochloric acid and then with water. The organic phase was dehydrated with anhydrous magnesium sulfate, and then the solvent was recovered to obtain 1.70 g of a viscous product. The viscous product was refined from a solvent of ether:hexane=5:3 to obtain an objective compound having a melting point of 134° to 135.5° C. in the form of a white crystal.

Infrared Absorption Spectrum (KBr Method) 1740 cm$^{-1}$, 1335 cm$^{-1}$, 1164 cm$^{-1}$

EXAMPLE 4 TO 19

Generally following the procedures described in Example 1 to 3, Compound Nos. 4 to 19 were prepared.

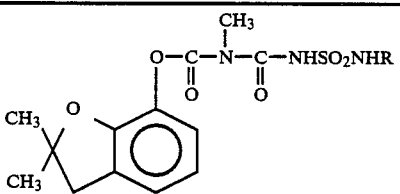

| Compound No. | R | Melting Point (°C.) | IR cm$^{-1}$ |
|---|---|---|---|
| 4 | —CH(CH$_3$)CH$_3$ | 139 to 141 | 1737, 1335, 1152 |
| 5 | —C$_4$H$_9$(n) | 92 to 93.5 | 1740, 1335, 1164 |
| 6 | —CH$_2$CH=CH$_2$ | 106 to 108 | 1737, 1335, 1164 |

-continued $$\text{structure: 2,2-dimethylbenzofuran-7-yl } O-C(=O)-N(CH_3)-C(=O)-NHSO_2NHR$$

| Compound No. | R | Melting Point (°C.) | IR cm$^{-1}$ |
|---|---|---|---|
| 7 | —CH$_2$C≡CH | 127 to 128.5 | 1734, 1335, 1164 |
| 8 | (4-Cl-phenyl) | 125 to 127 | 1737, 1332, 1158 |
| 9 | (4-OCH$_3$-phenyl) | 140 to 141.5 | 1734, 1335, 1158 |
| 10 | (4-COOCH$_3$-phenyl) | 131 to 133 | 1748, 1335, 1164 |
| 11 | (4-COOC$_2$H$_5$-phenyl) | 146 to 147.5 (Decomposed) | 1737, 1338, 1170 |
| 12 | (thiazol-2-yl) | 155 to 156 (Decomposed) | 1734, 1338, 1155 |
| 13 | (pyridin-2-yl) | 154.5 to 156 (Decomposed) | 1731, 1332, 1155 |
| 14 | —OCH$_3$ | 145 to 148 | 1728, 1341, 1173 |
| 15 | —C$_3$H$_7$ | 138 to 140 | 1737, 1335, 1155 |
| 16 | —C$_4$H$_9$(sec) | 125 to 126 | 1740, 1335, 1161 |
| 17 | —C$_4$H$_9$(t) | 154 to 156 | 1737, 1335, 1161 |
| 18 | (cyclopentyl) | 145 to 147 | 1728, 1332, 1164 |
| 19 | (cyclohexyl) | 140 to 142 | 1737, 1335, 1161 |

The compounds of this invention may be used directly as insecticides. However, it is generally convenient to use them in the form of emulsifiable concentrate, wettable powder, dust, fine granules, granules or impregnant to natural or synthetic materials.

In formulation of effective compounds, liquid or solid carriers may be used. Various organic solvents may be used as the liquid carriers, preferable examples being xylene, chlorobenzene, methylnaphthalene, cyclohexanone, isophorone, alcohols, dimethylformamide and N-methylpyrrolidone. Examples of solid carriers include kaoline, talc, bentonite, diatomaceous earth and clay, and synthetic compounds, such as alumina, zeolite and silicates, may also be used. In preparation of these formulations, various adjuvants, such as emulsifiers, dispersing agents, spreaders, humidifiers or penetrants, may be added for the purpose of emulsification, dispersion, suspension and penetration.

Formulation Examples and Test Examples, wherein the compounds of this invention are used, will now be described. However, it is noted that the invention is not limited by the following Examples. In the following Examples, "part" stands for "part by weight".

FORMULATION EXAMPLE 1

Emulsifiable Concentrate 20 parts of isophorone and 60 parts of xylene were added to 15 parts of Compound No. 5 and further an emulsifier composed of 1.5 parts of polyoxyethylene alkylether, 2 parts of alkylbenzenesulfonate and 1.5 parts of polyoxyethylenesorbitan alkylate was added. By mixing the components, a 20% emulsifiable concentrate was prepared.

FORMULATION EXAMPLE 2

Wettable Powder 30 parts of Compound No. 4 was admixed with 2 parts of white carbon, and a dispersing humidifier composed of 3 parts of sodium alkylethersulfate and 2 parts of sodium dialkylnaphthalenesulfonate was added. The mixture was added with 63 parts of clay which acted as a pulverization adjuvant, and after well mixing, pulverized it to prepare a 30% wettable powder.

FORMULATION EXAMPLE 3

Granule 67 parts of clay and 26 parts of bentonite was added to 3 parts of Compound No. 3 and further a disintegrator composed of 0.5 parts of alkylbenzenesulfonate and 3.5 parts of sodium ligninesulfonate was added. After well mixing, water was added to the mixture which was then granulated, dried and regulated to prepare a 3% granule.

TEST EXAMPLE 1

10 ml of a 1000 ppm suspension of each sample compound (30% wettable powder) was poured into a pot in which rice plant (1.5 leaf stage) was grown, and the pot was placed in a greenhouse enclosed by glass. 3 days after applying the sample compound, the rice plant was covered by a cylindrical metal netting having a diameter of 7.5 cm and a height of 40 cm and 10 female adults of Green rice leafhopper (Nephotettix cincticeps) were released in the netting. The numbers of living and dead insects were checked 48 hours after applying. The test was repeated twice. The results are shown in Table 1.

TABLE 1

| Compound No. | Mortality (%) | Compound No. | Mortality (%) |
|---|---|---|---|
| 1 | 100% | 12 | 100% |
| 2 | 100% | 13 | 100% |
| 3 | 100% | 14 | 100% |
| 4 | 100% | 15 | 100% |
| 5 | 100% | 16 | 100% |

TABLE 1-continued

| Compound No. | Mortality (%) | Compound No. | Mortality (%) |
|---|---|---|---|
| 7 | 100% | 17 | 100% |
| 8 | 90% | 18 | 80% |
| 9 | 90% | 19 | 80% |
| 10 | 90% | | |
| 11 | 90% | Control* | 100% |

*Control compound: 2,3-dihydro-2,2-dimethylbenzofuran-7-yl N-methylcarbamate

TEST EXAMPLE 2

30 ml of a 1000 ppm suspension of each sample compound (30% wettable powder) was poured into a pot in which cabbage (2 to 3 leaf stage) was grown, and the pot was placed in a greenhouse enclosed by glass. 3 days after applying the sample compound, the cabbage was covered by a cylindrical metal netting having a diameter of 7.5 cm and a height of 20 cm and 10 second instar larvae were released in the netting. 48 hours after applying the numbers of living and dead insects were checked. The test was repeated twice. The results are shown in Table 2.

TABLE 2

| Compound No | Mortality (%) |
|---|---|
| 1 | 100% |
| 2 | 100% |
| 3 | 100% |
| 4 | 100% |
| 5 | 100% |
| 7 | 100% |
| 15 | 100% |
| 16 | 100% |
| 17 | 100% |
| Control* | 100% |

*Control compound: 2,3-Dihydro-2,2-dimethylbenzofuran-7-yl N-methylcarbamate

TEST EXAMPLE 3

A predetermined quantity of a 3% granule of each compound was mixed with a soil contaminated with Southern root-knot nematode (Meloidogyne incognita). 2 days after treatment of the compound, 3 to 4 leaf stage tomato seedlings were transplanted, and the root-knot index was checked 25 days later. The results are shown in Table 3.

The root-knot index was determined with the following standard for nemotoidal evaluation.

0 No root-knots found
1 Few root-knots found
2 Moderate number of root-knots found
3 Many root-knots found
4 Very many root-knots found

TABLE 3

| Compound No. | Root-Knot Index Active Ingredient 500 g/a | Root-Knot Index Active Ingredient 250 g/a |
|---|---|---|
| 1 | 1 | 2 |
| 2 | 2 | 3 |
| 3 | 1 | 2 |
| 4 | 1 | 2 |
| 5 | 1 | 2 |
| 7 | 1 | 2 |
| 8 | 2 | 3 |
| 9 | 2 | 3 |
| 10 | 1 | 2 |
| 11 | 2 | 3 |
| 12 | 2 | 3 |
| 13 | 2 | 3 |
| 14 | 2 | 3 |
| 15 | 1 | 2 |
| 16 | 1 | 2 |
| 17 | 1 | 2 |
| Control* | 3 | 4 |

*Control compound: Bis(2-chloro-1-methylethyl)ether

TOXICITY TEST EXAMPLE

Representative examples of the compound of this invention were administered orally to mice ( ♂ ) and the acute toxicities thereof were tested. $LD_{50}$ was calculated from the percentage of dead mice according to the Litchfield-Wilcoxon Method 7 days after the administration. The results are set forth below.

| Compound No. | $LD_{50}$ (mg/kg) |
|---|---|
| 3 | 170 |
| 5 | 200 |
| Control* | 5 |

*Control compound: 2,3-dihydro-2,2-dimethylbenzofuran-7-yl N-methylcarbamate

By the use of the compounds of this invention, it is possible to prepare stable insecticides which are improved in insecticidal activity to control various harmful insects and yet reduced in toxicity to warm-blooded animals and fishes.

We claim:

1. A derivative of 2,3-dihydro-2,2-dimethylbenzofuran-7-yl N-(substituted sulfonylcarbamoyl) N-methylcarbamate represented by the general formula:

$$\text{(structure shown)} \quad O-C-N(CH_3)-C(=O)-NHSO_2X$$

wherein X stands for a halogen atom or —NHR where R is an alkyl group, cycloalkyl group, lower alkenyl group, lower alkynyl group, $$\text{phenyl-Z}$$

(where Z is a hydrogen atom, halogen atom, alkyl group, alkoxy group or alkoxycarbonyl group), aralkyl group, a 5-member or 6-member heterocyclic group, or an alkoxy group.

2. The derivative according to claim 1 which is 2,3-dihydro-2,2-dimethylbenzofuran-7-yl N-(chlorosulfonylcarbamoyl) N-methylcarbamate.

3. The derivative according to claim 1 which is 2,3-dihydro-2,2-dimethylbenzofuran-7-yl N-(methylsulfamoylcarbamoyl) N-methylcarbamate.

4. The derivative according to claim 1 which is 2,3-dihydro-2,2-dimethylbenzofuran-7-yl N-(ethylsulfamoylcarbamoyl) N-methylcarbamate.

5. The derivative according to claim 1 which is 2,3-dihydro-2,2-dimethylbenzofuran-7-yl N-(propylsulfamoylcarbamoyl) N-methylcarbamate.

6. The derivative according to claim 1 which is 2,3-dihydro-2,2-dimethylbenzofuran-7-yl N-(sec-butylsulfamoylcarbamoyl) N-methylcarbamate.

7. An insecticidal composition containing an insecticidally effective amount a derivative of 2,3-dihydro-2,2-dimethylbenzofuran-7-yl N-(substituted sulfonylcarbamoyl)-N-methylcarbamate represented by the general formula:

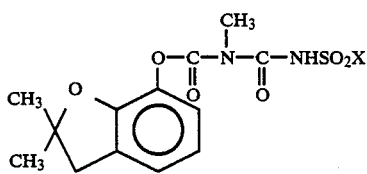

wherein X stands for a halogen atom or —NHR where R is an alkyl group, cycloalkyl group, lower alkenyl group, lower alkynyl group,

(where Z is a hydrogen atom, halogen atom, alkyl group, alkoxy group or alkoxycarbonyl group), aralkyl group, a 5-member or 6-member heterocyclic group, or an alkoxy group, mixed with a carrier suitable for insecticides.

8. The insecticidal composition according to claim 7 which contains 2,3-dihydro-2,2-dimethylbenzofuran-7-yl N-(chlorosulfonylcarbamoyl) N-methylcarbamate as an effective component.

9. The insecticideal composition according to claim 7 which contains 2,3-dihydro-2,2-dimethylbenzofuran-7-yl N-(methylsulfamoylcarbamoyl) N-methylcarbamate as an effective component.

10. The insecticidal composition according to claim 7 which contains 2,3-dihydro-2,2-dimethylbenzofuran-7-yl N-(ethylsulfamoylcarbamoyl) N-methylcarbamate as an effective component.

11. The insecticidal composition according to claim 7 which contains 2,3-dihydro-2,2-dimethylbenzofuran-7-yl N-(propylsulfamoylcarbamoyl) N-methylcarbamate as an effective component.

12. The insecticidal composition according to claim 7 which contains 2,3-dihydro-2,2-dimethylbenzofuran-7-yl N-(sec-butylsulfamoylcarbamoyl) N-methylcarbamate as an effective component.

* * * * *